(12) United States Patent
Abbott

(10) Patent No.: US 8,776,626 B2
(45) Date of Patent: Jul. 15, 2014

(54) PNEUMATIC MOTOR FOR OSCILLATORY MOTION

(76) Inventor: Brian F. Abbott, Fort Worth, OR (US)

( * ) Notice: Subject to any disclaimer, the term of this patent is extended or adjusted under 35 U.S.C. 154(b) by 464 days.

(21) Appl. No.: 13/269,469

(22) Filed: Oct. 7, 2011

(65) Prior Publication Data

US 2012/0179186 A1    Jul. 12, 2012

Related U.S. Application Data

(60) Provisional application No. 61/391,047, filed on Oct. 7, 2010.

(51) Int. Cl.
*F16H 23/00* (2006.01)
*A61M 37/00* (2006.01)

(52) U.S. Cl.
CPC ............................... *A61M 37/0076* (2013.01)
USPC .............................................................. 74/60

(58) Field of Classification Search
USPC ............................. 74/60, 25; 81/9.22; 60/370
See application file for complete search history.

(56) References Cited

U.S. PATENT DOCUMENTS 4,408,623 A * 10/1983 Murray ......................... 132/73.6
5,725,058 A *  3/1998 Eriksson ....................... 173/114

* cited by examiner

*Primary Examiner* — Edward Look
*Assistant Examiner* — Daniel Collins
(74) *Attorney, Agent, or Firm* — Geoffrey Dobbin; Dobbin IP Law P.C.

(57) ABSTRACT

The present invention is a pneumatically driven oscillatory motor. It features fan gear with an eccentrically mounted hub which imparts a wobbling motion on a bearing and associated collar. This wobbling motion then translated in to a vertical oscillatory motion of a collar arm extending radially from said collar. Additional structures to direct flow of expelled air are also provided. The collar arm may be removable from the collar. The motor has many applications where oscillatory motion is required, such as in tattoo needles.

14 Claims, 7 Drawing Sheets

PNEUMATIC MOTOR FOR OSCILLATORY MOTION

CROSS-REFERENCES TO RELATED APPLICATIONS

The present Application claims priority as a non-provisional perfection of prior filed U.S. Provisional Application No. 61/391,047, filed Oct. 7, 2010, and incorporates the same by reference herein in its entirety.

FIELD OF THE INVENTION

The present invention relates to the field of oscillating drivers and more particularly relates to a pneumatically driven motor that may be used for oscillatory motion in devices such as one used to operate a tattoo needle.

BACKGROUND OF THE INVENTION

Repetitive, oscillatory motion has been used in many circumstances for useful machines, ranging from clocks to hammers. Producing oscillatory motion has, therefore, been the purpose of a large number of devices created for a time-span measuring centuries. Efficient designs have numerous uses in today's, and future, technological arts.

Likewise, the art of tattooing the human body has been known for at least six millennia. The process involves the insertion of indelible ink into the dermis layer of the skin. Once there, the ink stains the dermis and is permanently protected by and visible through the epidermal layer. Since the practice of tattooing requires repeated insertion of a needle to create a solid line, the process has been adapted in modern times to include the use of a hand-held needle driver that oscillates a needle or set of needles 80 to 150 times a second. An efficient oscillating motor, then, can improve the technological art.

The present invention is a pneumatically driven oscillating motor that has numerous applications, including for use in a tattoo needle machine. The motor is utilizes an eccentrically mounted hub, which produces the necessary oscillatory motion.

SUMMARY OF THE INVENTION

This invention provides a pneumatically driven oscillatory motor. As such, the present invention's general purpose is to provide a new and improved oscillatory motor that is small, efficient and economical. To accomplish these objectives, the motor comprises a fan gear that is driven by a moving column of air. The fan gear in turn rotates an axle onto which is attached an eccentrically mounted hub. This hub is likewise connected to a bearing which is in turn positioned underneath a coaxially mounted collar. As the axel and hub rotate, an eccentric motion generated, causing the bearing to repeatedly raise and lower the collar. In the case of a tattoo needle machine, the needle is mounted upon an arm projecting from the collar.

The more important features of the invention have thus been outlined in order that the more detailed description that follows may be better understood and in order that the present contribution to the art may better be appreciated. Additional features of the invention will be described hereinafter and will form the subject matter of the claims that follow.

Many objects of this invention will appear from the following description and appended claims, reference being made to the accompanying drawings forming a part of this specification wherein like reference characters designate corresponding parts in the several views.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE PREFERRED EMBODIMENT

With reference now to the drawings, the preferred embodiment of the pneumatic oscillatory motor is herein described. It should be noted that the articles "a", "an", and "the", as used in this specification, include plural referents unless the content clearly dictates otherwise.

Figure 1:
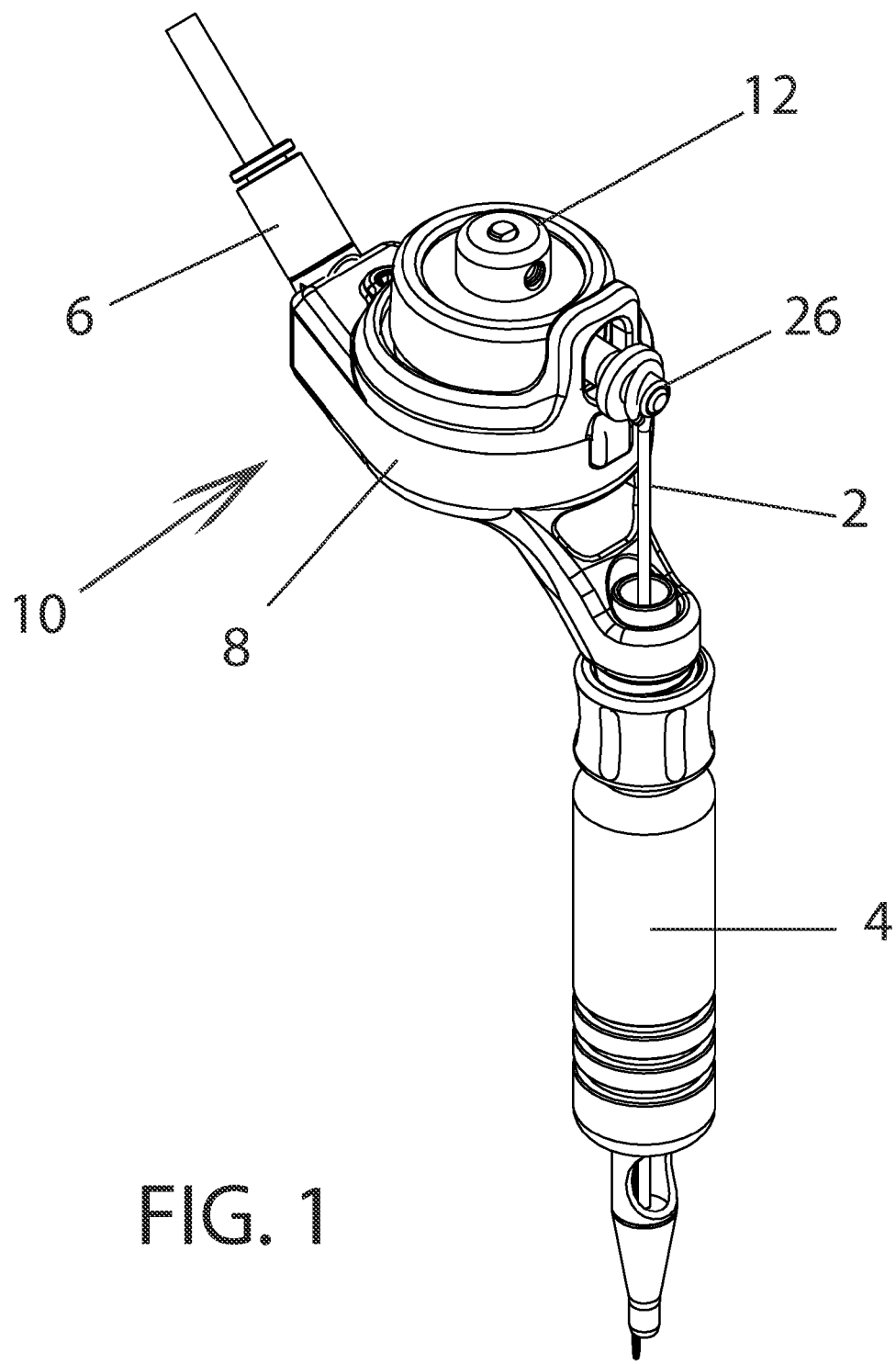
FIG. 1 is a perspective view of a pneumatically driven motor according to the present invention being utilized in a tattoo needle machine.
Figure 2:
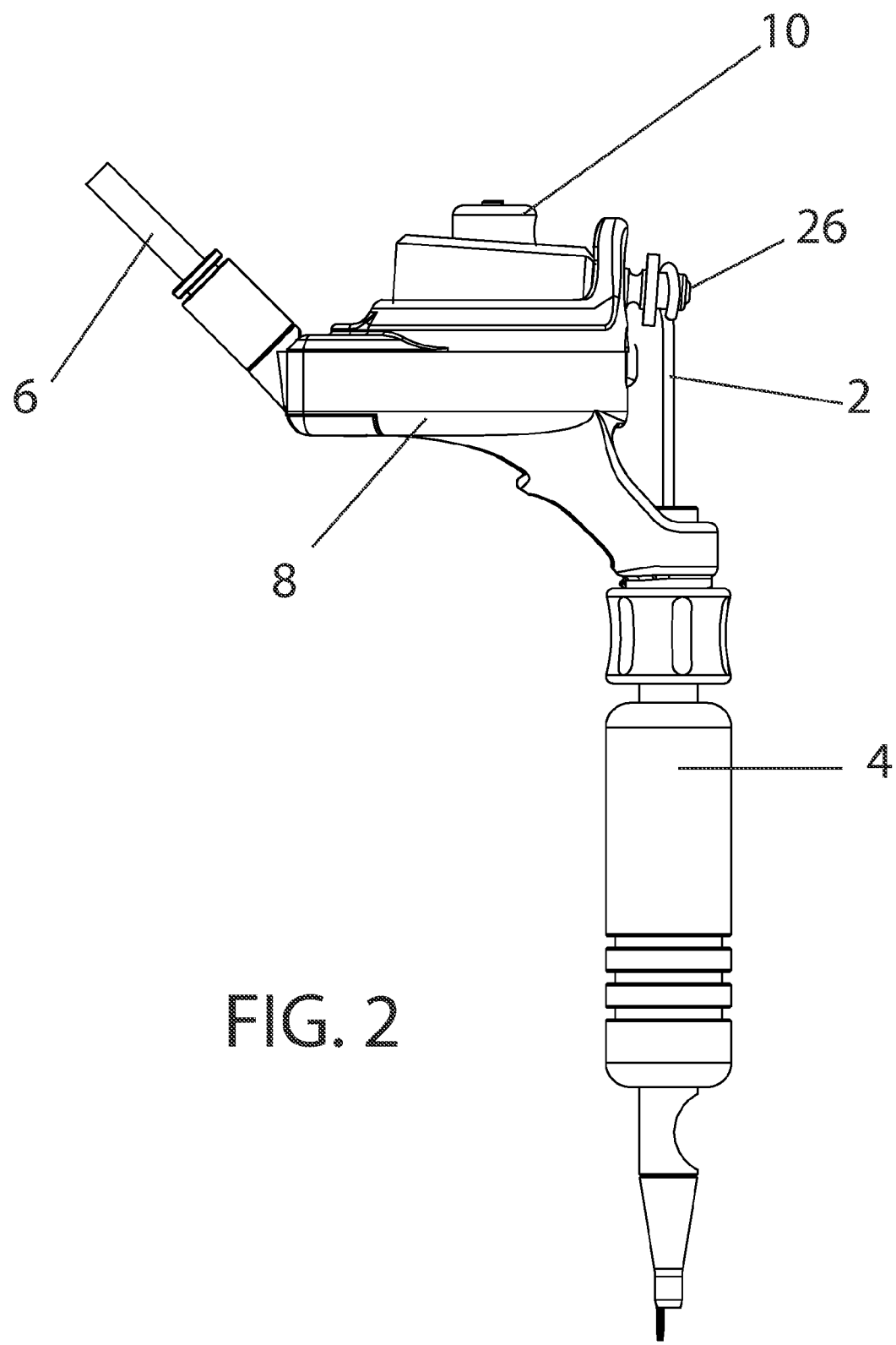
FIG. 2 is a side elevation of the assembly of FIG. 1
Figure 3:
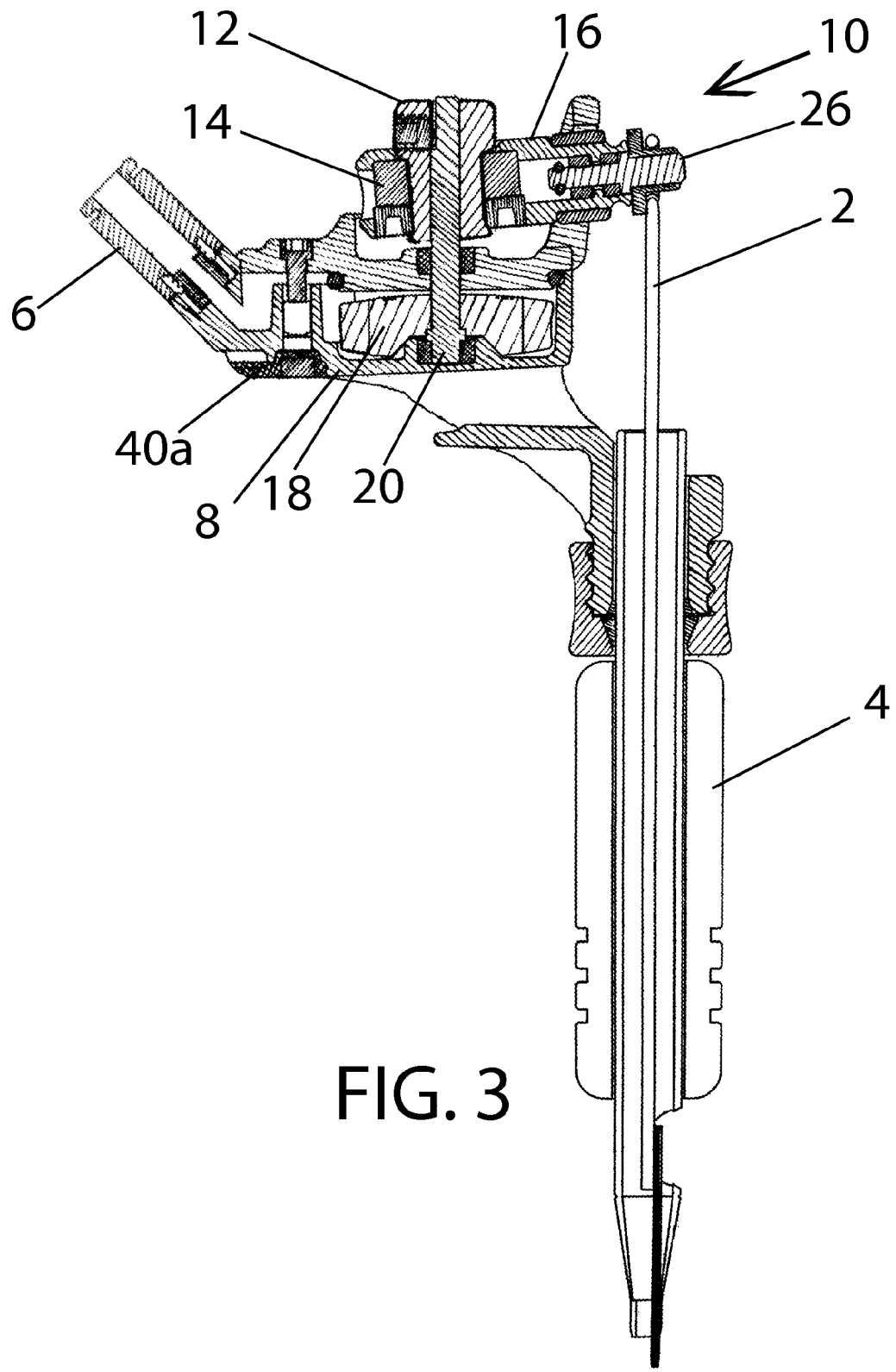
FIG. 3 is a sectional view of the assembly of FIG. 1.
Figure 4:
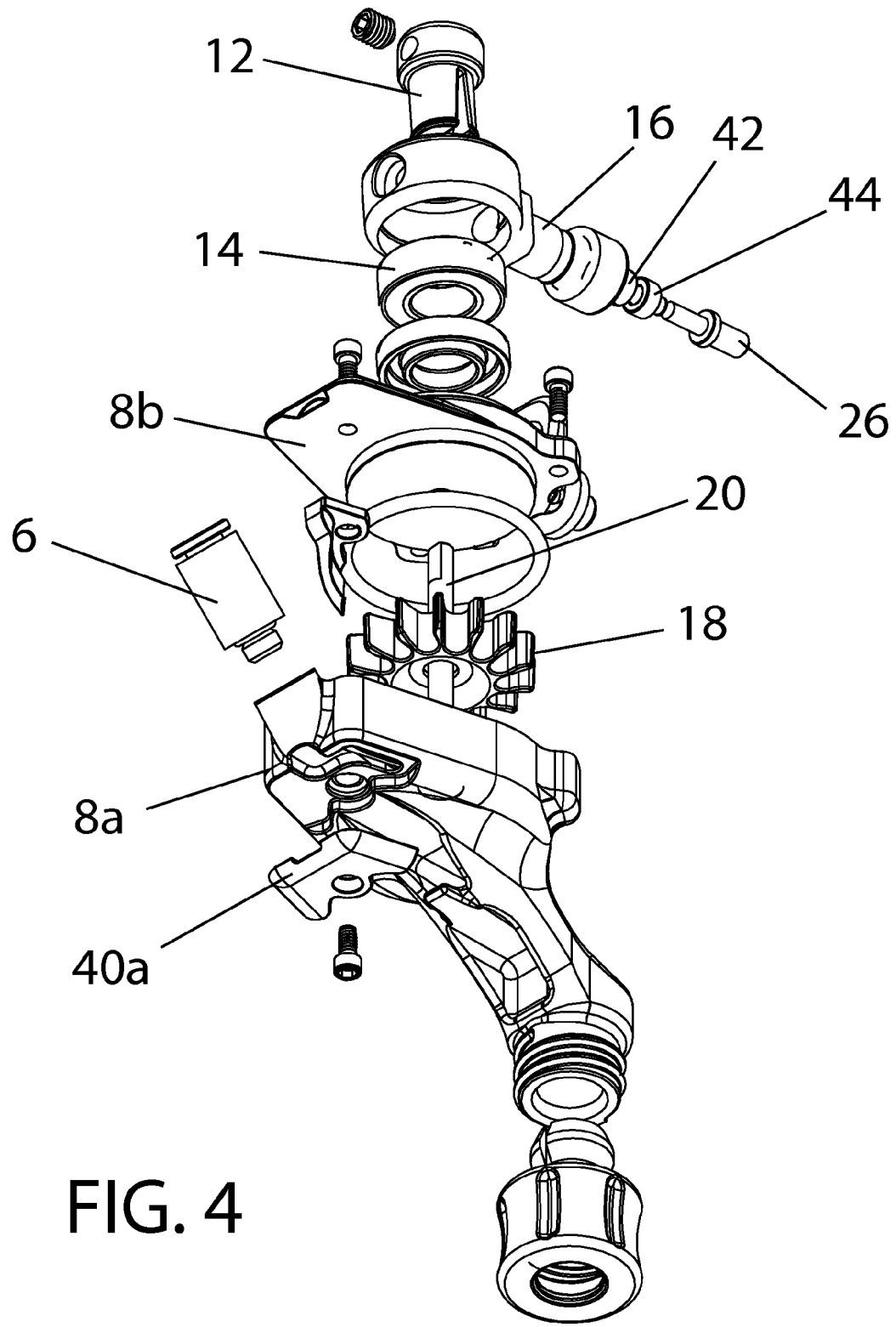
FIG. 4 is an exploded view of the motor utilized in FIG. 1
Figures 5, 6:
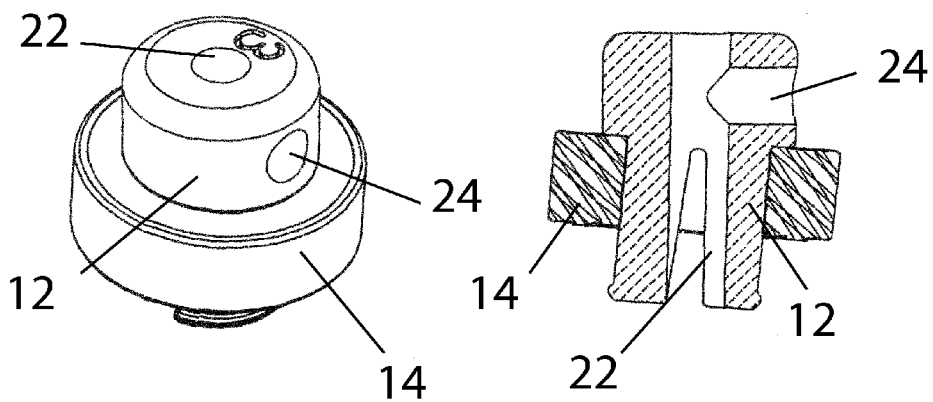
FIG. 5 is a perspective view of the hub utilized in the motor of FIG. 4.
FIG. 6 is sectional view of the hub of FIG. 5.
Figure 9:
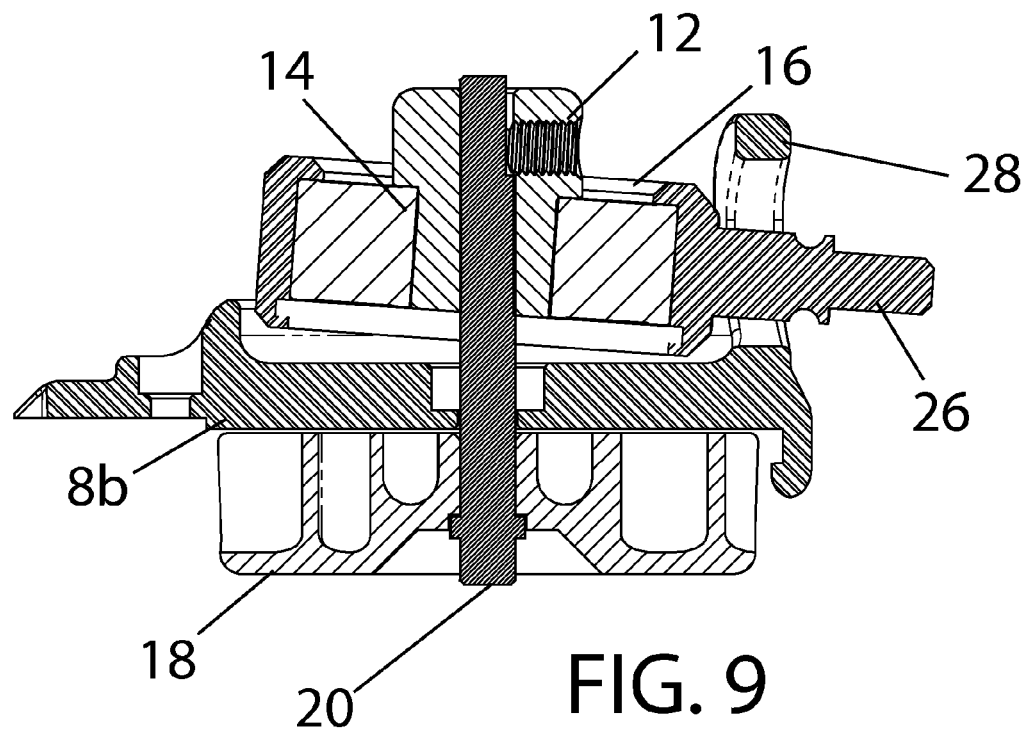
FIG. 9 is a sectional view of the motor assembly of FIG. 4, with the upper housing.

With reference to FIGS. 1-3, the motor 10 in its most basic form is shown in the setting of a tattoo needle assembly. As seen in FIG. 1, the needle 2 resides in handle 4 and is mounted upon collar arm 26 of the motor 10. Pneumatic tubing carries a column of air into the inlet 6 of the motor 10. The exploded view, FIG. 4, details the assembly of the motor 10. A fan gear 18 resides in the housing 8, which is assembled from two components 8a, 8b, and is attached to an axle 20. The axle 20 extends through the motor 10 and features a hub 12 at the end of the axle opposite the fan gear 18. As seen in FIGS. 5 and 6, the hub 12 features an eccentric, non-coaxial, shaft 22 into which axle 20 is inserted. A bolt is inserted through tap 24 to secure hub 12 to axle 20. A bearing 14 resides about hub 12 and supports collar 16. The bearing 14 reduces rotational moments of the hub 12 on the collar 16 and helps the collar arm 26 remain in one position relative to the upper housing 8*b*. Due to their eccentric relation, as the axle 20 rotates, the hub 12 will have an eccentric rotational motion, or wobble. This wobble is then imparted to the bearing 14 adjacent and beneath the hub 12, which in turn causes wobble in the collar 16 adjacent bearing 14. As shown in FIG. 9, collar arm 26 extends from collar 16 and through guard 28 of upper housing 8*b*. As collar 16 wobbles, it causes a net vertical oscillatory motion in collar arm 26. Guard 28 serves the dual purposes of keeping collar arm 26, and the associated needle 2, centered over the bore of the handle 4 and of keeping objects away from the oscillating collar arm 26.

Figure 10:
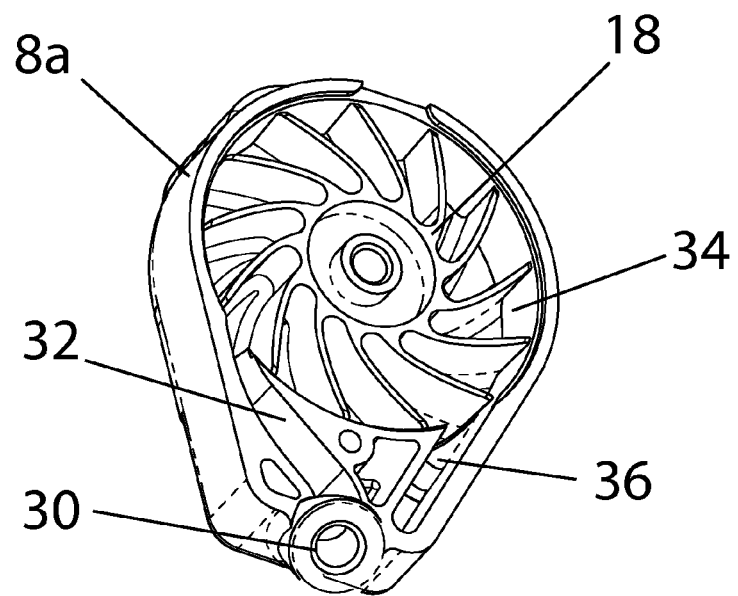
FIG. 10 is another perspective view of the lower housing.
Figure 11:
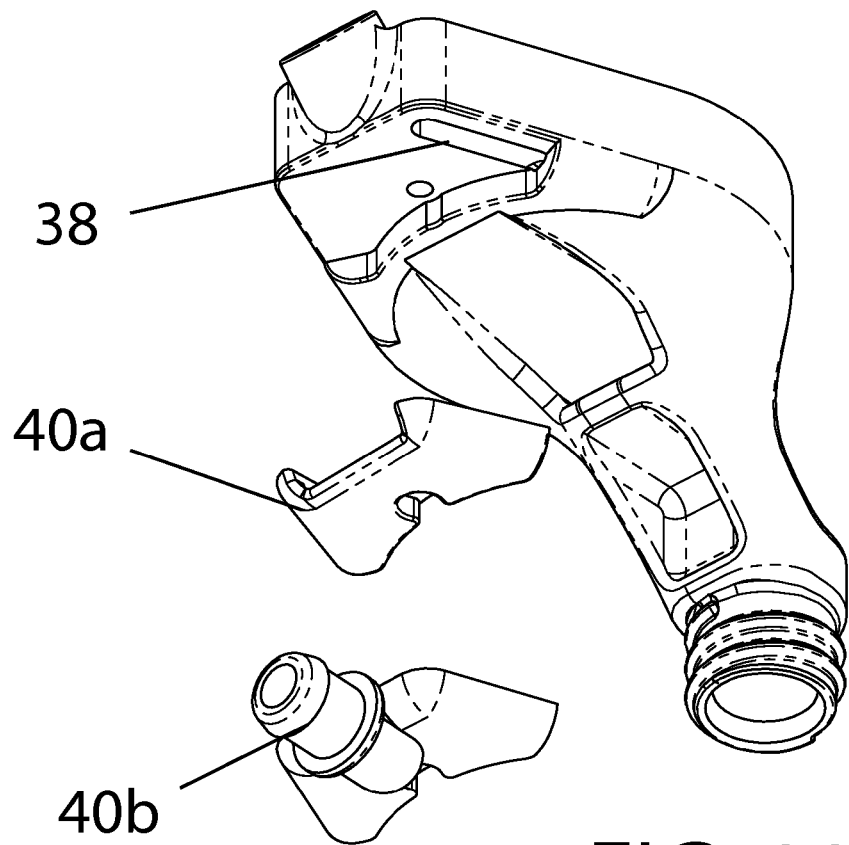
FIG. 11 is a perspective view of the lower housing of FIG. 10, with two alternate vent plates.
Figure 12:
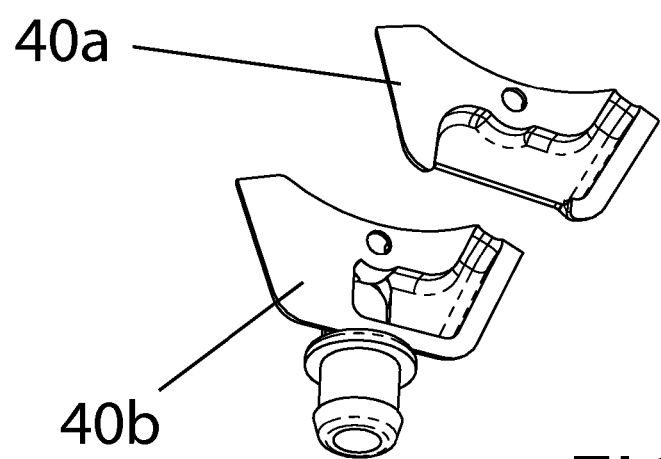
FIG. 12 is an upper perspective view of the vent plates of FIG. 11.

Airflow is directed into the lower housing 8*a* at port 30, shown in FIG. 10. Together, the housing components 8*a*, 8*b* create a virtually airtight housing, except two passages 32, 36 in the lower housing 8*a*. The direction of the airflow is then governed by these passages as ingress passage 32 is a direct extension of port 30 and egress passage 36 terminates at a vent 38 (FIG. 11). In this manner, airflow is forced to travel in one direction through gear cavity 34, rotating fan gear 18. The airflow may be directed out of the vent 38 through a venting structure, such as the simple directional vent plate 40*a* or the alternate vent plate with a tube attachment 40*b*. Either plate is attachable to the housing with a bolt and channels the airflow through its particular structure, as shown in FIG. 12, according to the desires of the user. Other venting structures may be crafted based on the principles of these two plates 40*a*, 40*b* and they should not be seen as limiting.

Figures 7, 8:
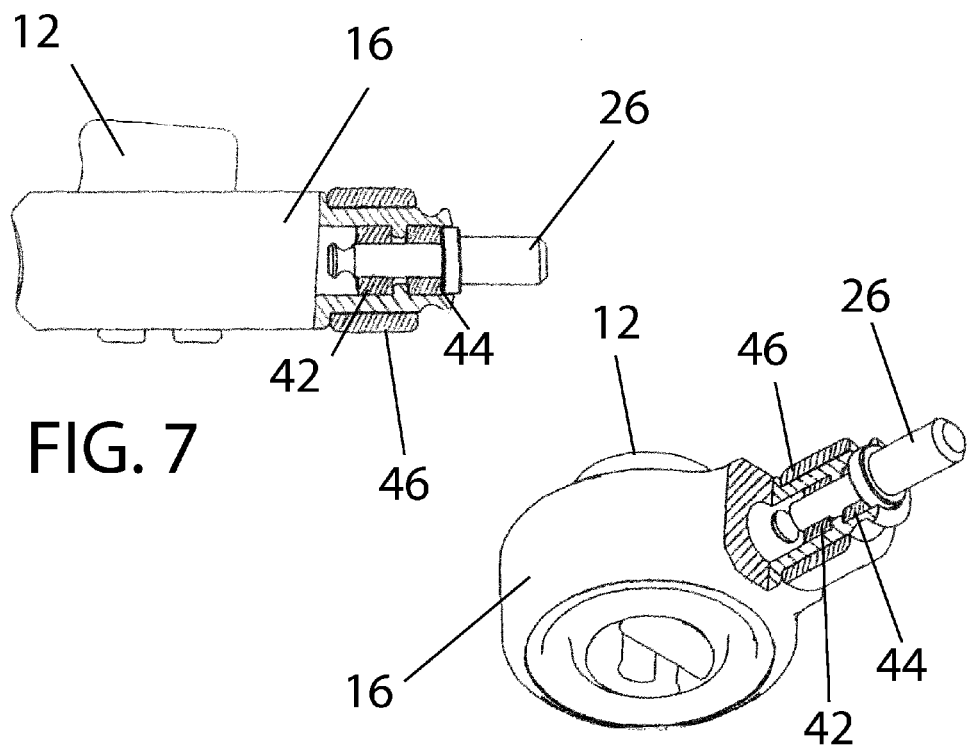
FIG. 7 is a side elevation of the hub and collar of the assembly of FIG. 1, in partial section.
FIG. 8 a perspective view of the hub and collar of the assembly of FIG. 1, in partial section.

One further improvement is the use of a separable collar arm 26, shown in FIGS. 7 and 8. The separable collar 26 is inserted in the collar 16 and is secured by two bearings 42, 44. The use of a separable collar arm 26, as secured by the bearings 42, 44, reduces friction and allows the collar arm 26 to be inserted into the collar 16 after the collar 16 is secured on the upper housing 8*b*. However, it is to be understood that collar arm 26 may be of a single piece with collar 16. An additional bearing 46 also may be added as a shield over the collar 16.

Although the present invention has been described with reference to preferred embodiments, in particular with a tattoo needle machine, numerous modifications and variations can be made, including uses in other oscillatory machines, and still the result will come within the scope of the invention. It is to be appreciated that various structures for the housing assembly, including the inclusion of gaskets, bearings, and directional structures are also possible, as are various structures for the hub. No limitation with respect to the specific embodiments disclosed herein is intended or should be inferred.

What is claimed is:
1. A pneumatically driven oscillatory motor comprising:
   a. a housing, the housing further comprising an air column defined by:
      i. an air inlet
      ii. an air outlet
      iii. a gear chamber disposed between the air inlet and air outlet in the air column;
   b. a fan gear located in the gear chamber and serving as a portion of the air column;
   c. an axle, coaxially mounted on the fan gear and extending through an opening of the housing;
   d. a hub with an eccentric shaft, mounted upon an end of the axle opposite the fan gear;
   e. a bearing situated about the hub; and
   f. a collar positioned over the bearing, said collar having a collar arm extending radially therefrom;
   wherein, upon rotation of the fan gear, rotation is imparted to the axle and the associated hub , which then rotates eccentrically, causing a wobbling effect on the bearing and associated collar which then imparts an oscillating vertical motion upon the collar arm.

2. The oscillatory motor of claim 1 further comprising a guard, extending from the housing and encircling the collar arm.

3. The oscillatory motor of claim 2, further comprising interchangeable vent structures designed to fit over the air outlet.

4. The oscillatory motor of claim 3, further comprising a collar arm that is removable from the collar.

5. The oscillatory motor of claim 1, further comprising interchangeable vent structures designed to fit over the air outlet.

6. The oscillatory motor of claim 5, further comprising a collar arm that is removable from the collar.

7. The oscillatory motor of claim 1, further comprising a collar arm that is removable from the collar.

8. A tattoo needle machine comprising the pneumatically driven oscillatory motor of claim 1.

9. A tattoo needle machine comprising the pneumatically driven oscillatory motor of claim 2.

10. A tattoo needle machine comprising the pneumatically driven oscillatory motor of claim 3.

11. A tattoo needle machine comprising the pneumatically driven oscillatory motor of claim 4.

12. A tattoo needle machine comprising the pneumatically driven oscillatory motor of claim 5.

13. A tattoo needle machine comprising the pneumatically driven oscillatory motor of claim 6.

14. A tattoo needle machine comprising the pneumatically driven oscillatory motor of claim 7.

* * * * *